United States Patent [19]

Halbo

[11] Patent Number: 6,012,344
[45] Date of Patent: Jan. 11, 2000

[54] INSPECTION MACHINE FOR CONTAINERS

[75] Inventor: Hansjoerg Halbo, Neutraubling, Germany

[73] Assignee: Krones AG Hermann Kronseder Maschinenfabrik, Neutraubling, Germany

[21] Appl. No.: 08/930,207

[22] PCT Filed: Feb. 11, 1997

[86] PCT No.: PCT/EP97/00623

§ 371 Date: Feb. 17, 1998

§ 102(e) Date: Feb. 17, 1998

[87] PCT Pub. No.: WO97/30343

PCT Pub. Date: Aug. 21, 1997

[30] Foreign Application Priority Data

Feb. 13, 1996 [DE] Germany .......................... 196 05 133

[51] Int. Cl.[7] .......................... G01N 21/90; G01M 19/00
[52] U.S. Cl. ................ 73/865.8; 250/223 B; 356/239.4; 198/339.1
[58] Field of Search ................ 73/865.8, 865.9; 250/223 B; 356/240.1, 239.4, 239.5; 198/339.1

[56] References Cited

U.S. PATENT DOCUMENTS

| | | | |
|---|---|---|---|
| 3,651,937 | 3/1972 | Kronseder | 250/223 B X |
| 4,020,949 | 5/1977 | Erdman | 250/223 B |
| 4,021,122 | 5/1977 | Krenmayr | 250/223 B X |
| 4,221,961 | 9/1980 | Peyton | 250/223 B |
| 4,636,635 | 1/1987 | Krönsedar | 250/233 B |
| 4,731,649 | 3/1988 | Chang et al. | 250/223 B X |
| 4,790,662 | 12/1988 | Bischkopf et al. | 250/223 B X |
| 4,934,510 | 6/1990 | Lutgendorf | 198/461.3 |
| 5,414,777 | 5/1995 | van der Schaar et al. | 356/239.4 X |
| 5,505,312 | 4/1996 | Haring et al. | 209/524 |
| 5,546,819 | 8/1996 | Zodrow | 73/865.8 |

FOREIGN PATENT DOCUMENTS

| | | |
|---|---|---|
| 186278 | 7/1986 | European Pat. Off. . |
| 415154 | 3/1991 | European Pat. Off. . |
| 487402 | 5/1992 | European Pat. Off. . |
| 4127702 | 2/1993 | Germany . |
| 9310623 | 12/1993 | Germany . |

OTHER PUBLICATIONS

Abstract of JP 9–271734 dated Oct. 21, 1997 by Yoshimitsu et al by, JPO JP409271734A copyright 1997 and Derwent Information Ltd, Acc–No.–1998–003328, week 199801, copyright 1998.

*Primary Examiner*—Thomas P. Noland
*Attorney, Agent, or Firm*—Flynn, Thiel, Boutell & Tanis, P.C.

[57] ABSTRACT

In an inspection machine for containers comprising a feed conveyor, a discharge conveyor, and an intermediate conveyor which is arranged thereinbetween and transfers the containers without any self-rotation, and a rotary conveyor which imparts a rotational movement to the containers and is provided at the feed conveyor, a first side inspection device is arranged at the feed conveyor in front of the rotary conveyor, a second side inspection device is arranged at the discharge conveyor after the intermediate conveyor, and a bottom inspection device is arranged in the area of the gap existing between the feed conveyor and the discharge conveyor. A very efficient container transport and a high inspection accuracy are achieved with such an assembly.

19 Claims, 1 Drawing Sheet

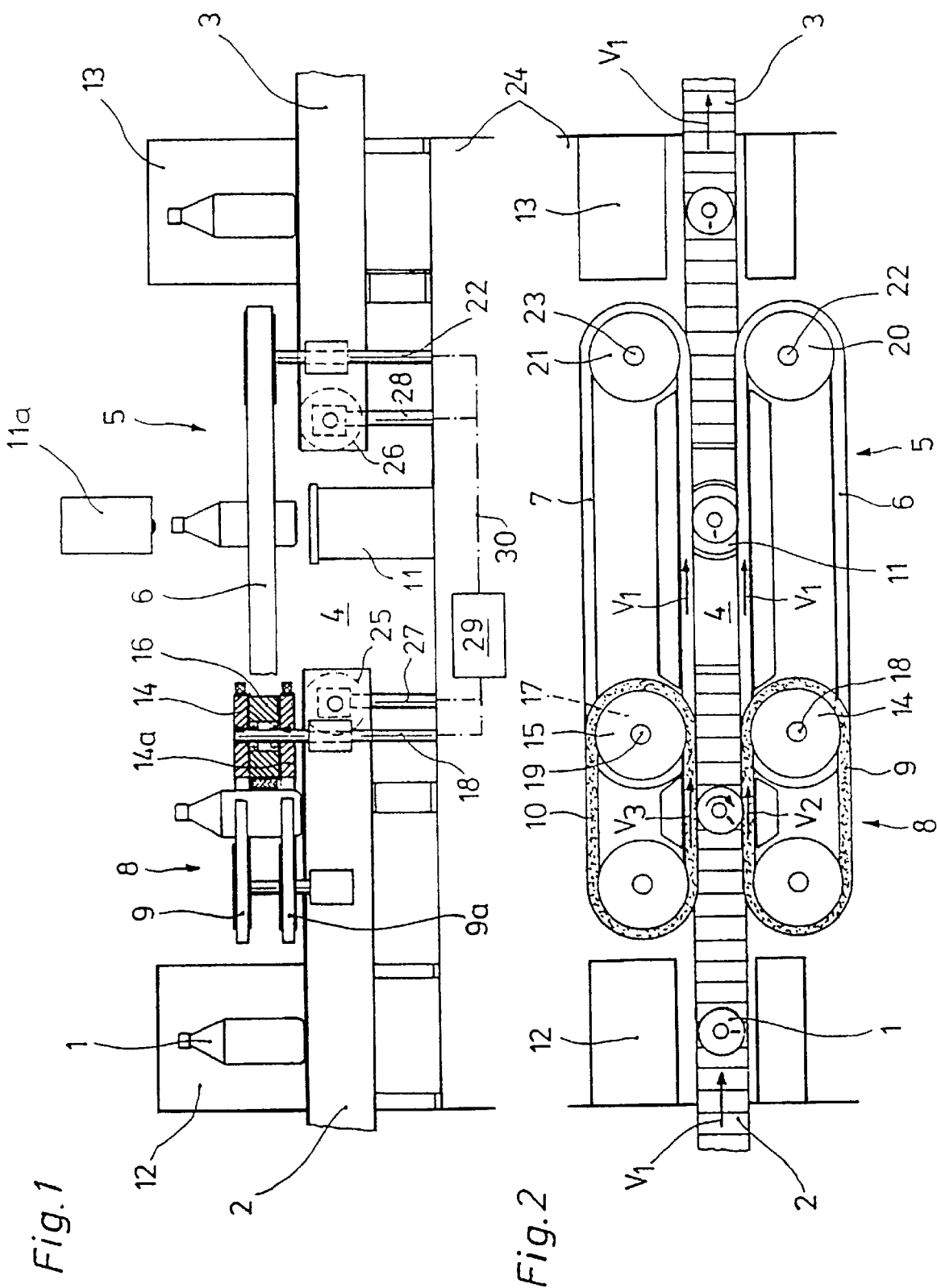

INSPECTION MACHINE FOR CONTAINERS

FIELD OF THE INVENTION

The present invention relates to an inspection machine for containers including a feed conveyor, an intermediate conveyor and a discharge conveyor.

BACKGROUND OF THE INVENTION

Use has already been made of such a type of inspection machine, wherein the rotary conveyor which operates with a driven endless conveying means and an opposite stationary friction surface is arranged at the feed conveyor at a distance in front of the intermediate conveyor, namely in the operative area of the single side-inspection device. Being of a compact construction, this prior-art inspection machine makes it possible to check containers for impurities, faults, etc., in both the bottom area and the wall area. The containers are handed over in a safe upright position to the discharge conveyor by the conveying means of the intermediate conveyor which are driven at the same speed. A disadvantage is, however, that the rotary conveyor can only engage the lowermost wall portion of the containers in order to avoid an excessively restricted field of vision of the side inspection device. Moreover, since a great rotary angle is required over a relatively short transportation path, the container transport in the area of the rotary conveyor is extremely unstable and the inspection result does not meet the requirements. Moreover, the containers might very easily tip over before being gripped by the intermediate conveyor after their passage through the rotary conveyor. The prior-art inspection machine is therefore not suited for high capacities.

Furthermore, use is made of an inspection machine comprising a feed conveyor, a discharge conveyor spaced apart from the feed conveyor, and an intermediate conveyor transferring the containers between feed conveyor and discharge conveyor, wherein a first side inspection device is arranged at the feed conveyor, a second side inspection device at the discharge conveyor and a bottom inspection device in the area of the gap existing between the feed conveyor and the discharge conveyor. The intermediate conveyor comprises two endless conveying means which engage opposite sides of the containers and are driven at different speeds and which rotate the containers traveling from the feed conveyor to the discharge conveyor by a specific angle. Hence, the containers are rotatingly fed from the intermediate conveyor to the discharge conveyor and can easily reel and tilt over. The consequence thereof is a damaged second side inspection device, as well as serious operational failures. Moreover, the function of the bottom inspection device may be impaired by the self-rotation of the containers in the area of the bottom inspection device.

It is therefore the object of the present invention to improve the inspection machine of the above-mentioned type with respect to efficiency and operational reliability of the container transport and with respect to inspection accuracy as far as side wall inspection is concerned.

SUMMARY OF THE INVENTION

In an inspection machine according to the invention, no rotation of the containers is observed during side inspection. The rotary conveyor can therefore engage the containers in the desired portions and for any desired length of time and can rotate the containers reliably and securely by the desired angle, i.e., also at high outputs. An important aspect is that the containers are standing on the feed conveyor during their self-rotation. A remaining angular momentum of the containers is braked upon entry into the intermediate conveyor at the latest, since the conveying means thereof rotate at an absolutely identical speed, thereby handing over the bottles without any angular momentum to the discharge conveyor.

Advantageous developments of the invention, which contribute each to a particularly safe container transport, are indicated in the subclaims.

Particular mention should be made of the inventive developments. As a result of the overlapping arrangement of rotary conveyor and intermediate conveyor with coaxial pulleys, as indicated therein, an uninterrupted transition of the containers from the rotary conveyor to the intermediate conveyor is made possible. The containers can therefore be rotated very quickly over a short distance and are directly received by the intermediate conveyor after their rotation and are braked, if necessary. The intermediate conveyor will then pass on the containers to the discharge conveyor without any rotation. This arrangement reliably prevents any reeling or even tilting of the containers that might be caused by the rotation of the containers.

BRIEF DESCRIPTION OF THE INVENTION

An embodiment of the present invention shall now be described in the following text with reference to drawings, in which:

FIG. 1 is a side view of an inspection machine;

FIG. 2 is a top view of the inspection machine shown in FIG. 1.

DETAILED DESCRIPTION OF THE INVENTION

The inspection machine according to FIGS. 1 and 2 is provided for checking upright returnable bottles which are made of glass and have a rotationally symmetrical basic shape, hereinafter called bottles 1, for contaminations and impurities in the area of the bottom and the side wall. The machine comprises a housing 24 whose upper side has arranged thereon a feed conveyor 2, a discharge conveyor 3, a rotary conveyor 8 and an intermediate conveyor 5 for conveying bottles 1 which pass in a straight line through the inspection machine.

The feed conveyor 2 as well as the discharge conveyor 3 which is aligned therewith have hinge band type chains which run over chain wheels 25, 26 and are driven by drive shafts 27, 28.

The hinge band type chains form horizontal conveying surfaces on which bottles 1 are standing in an upright position and are guided, if necessary, by lateral rails (not shown). A gap 4 the length of which is several times that of a bottle diameter is formed between the feed conveyor 2 and the discharge conveyor 3 which is arranged at a distance therefrom. A bottom inspection device 11 is seated in the gap 4 with a light source being arranged below bottles 1 and a camera 11a being disposed above bottles 1. Moreover, a first side inspection device 12 is arranged with a light source and a camera at feed conveyor 2, and a similar second side inspection device 13 is arranged at discharge conveyor 3. Bottles 1 are standing in the area of the two side inspection devices 12, 13 in a free manner and without any self-rotation on the hinge band type chains of the feed and discharge conveyors 2, 3 and can therefore be checked over their entire height in an unobstructed manner for contaminations, etc.

The first side inspection device 12 is followed by a rotary conveyor 8 which rotates the bottles 1 standing on the feed conveyor 2 by about 90 degrees. The wall portions which are oriented in the area of the first side inspection device 12 in and opposite to the direction of transportation are thereby rotated laterally outwardly, thus passing into the full range of vision of the second side inspection device 13. The rotary conveyors 8 have a total of four endless conveying means 9, 9a, 10, and a conveying means (not shown) below conveying means 10 in FIG. 2 corresponding to conveying means 9a, in the form of toothed belts which are provided on the outside with an elastic sponge rubber cover. The conveying means 9 to 10 are positioned in pairs one upon the other at opposite sides of the feed conveyor 2 in the area between the first side inspection device 12 and the gap 4 so that they elastically clamp thereinbetween the bottles 1 arriving from the first side inspection device 12 and release the bottles 1 again in front of gap 4. The conveying means 9 to 10 rotate in two horizontal planes and wind around pulleys of equal size, with the front pulleys 14, 14a and 15, and a front pulley (not shown) below pulley 15 in FIG. 2 and corresponding to pulley 14a in FIG. 1, being mounted at a distance and in superposed fashion on vertical drive shafts 18, 19. The upper conveying means 14 and 15 laterally engage bottles 1 in the upper body portion and the lower conveying means 14a and 15a laterally engage bottles 1 in the lower body portion, whereby the bottles are securely fixed, additionally supported by the hinge band type chain of the feed conveyor 2.

The two drive shafts 18, 19 for the conveying means 9 to 10 and the two drive shafts 27, 28 for the feed conveyor 2 and the discharge conveyor 3 are driven by a motor 29, which is seated in the housing 24, via a gear train 30, which is drawn in dash-dotted fashion, namely in synchronism with each other in such a manner that the feed conveyor 2 and the discharge conveyor 3 have the same speed V1. Speed V2 of the two right conveying means 9, 9a is smaller by a specific amount, and speed V3 of the two left conveying means 10, 10a is greater by the same amount than speed V1 of feed conveyor 2. Speeds V2 and V3 are chosen such that bottles 1 are rotated in the area of the rotary conveyor 8 by the desired rotary angle of about 90 degrees, with the center axis of the bottles being moved at speed V1. Therefore, bottles 1 are rotated about their own axis in a gentle and smooth manner, without any change in their translational movement.

The rotary conveyor 8 is followed by the intermediate conveyor 5 which bridges the gap 4 between the feed conveyor 2 and the discharge conveyor 3 and, to this end, covers the end portion of the feed conveyor 2 and the initial portion of the discharge conveyor 3. The intermediate conveyor 5 comprises two endless conveying means 6, 7 that are formed by toothed belts which have an elastic cover of sponge rubber provided on their outside. The two conveying means 6, 7 rotate in spaced-apart relationship in a horizontal plane, clamping therebetween the bottles 1 which have been released by the rotary conveyor 8. Bottles 1 are thus carried without any bottom support across gap 4 and through the bottom inspection device 11 and are then placed on discharge conveyor 3.

Each conveying means 6, 7 runs over two pulleys 16, 17, 20, 21, the two front pulleys 20, 21 being mounted on the vertical drive shafts 22, 23. Shafts 22, 23 are driven through the gear train 30 by motor 29 in synchronism with feed conveyor 2, discharge conveyor 3 and rotary conveyor 8 in such a manner that the two conveying means 6, 7 have exactly the same speed V1 as the feed conveyor 2 and the discharge conveyor 3. Hence, the bottles 1 pass over the bottom inspection device 11 without any self-rotation and are handed over to the discharge conveyor 3 without any objectionable angular momentum. A second undisturbed check of the wall is there carried out by the second side inspection device 13. The two rear pulleys 16, 17 of the intermediate conveyor 5 are supported on the drive shafts 18, 19 of the rotary conveyor 8 in a freely rotatable manner, namely between its pulleys 14 and 14a and pulley 15 and the corresponding pulley (not shown), respectively. The diameters of all pulleys and the thicknesses of the conveying means are adapted to one another such that the sides of the rotary conveyor 8 which run in the transportation direction pass smoothly into the sides of the intermediate conveyor 5 running in the transportation direction, where their rotation is braked. Moreover, since the two conveying means 6, 7 of the intermediate conveyor 5 engage the center portion of the bottle body, bottles 1 are transported in a smooth and stable manner by the rotary conveyor 8 and the intermediate conveyor 5. A very high transportation performance can therefore be achieved without bottles 1 running any risk of tilting.

What is claimed is:

1. In an inspection machine for containers, comprising a feed conveyor, a discharge conveyor, an intermediate conveyor which bridges a gap existing therebetween and comprises at least two endless conveying means drivable at the same speed for engaging opposite sides of containers and transferring containers without any rotation from said feed conveyor to said discharge conveyor, said inspection machine further comprising a rotary conveyor which is arranged at said feed conveyor and comprises at least one driven endless conveying means which laterally engages and rotates containers on said feed conveyor, a bottom inspection device arranged in an area of said gap, and a first side inspection device arranged in an area of said feed conveyor, the improvement wherein said first side inspection device is arranged upstream of said rotary conveyor and a second side inspection device is arranged downstream of said rotary conveyor.

2. The inspection machine according to claim 1, wherein said rotary conveyor rotates containers standing on said feed conveyor by an angle of about 90 degrees.

3. The inspection machine according to claim 1, wherein said first side inspection device is arranged in the area of said feed conveyor directly in front of said rotary conveyor.

4. The inspection machine according to claim 1, wherein said second side inspection device is arranged in an area of said discharge conveyor following said intermediate conveyor.

5. The inspection machine according to claim 1, wherein said intermediate conveyor follows said rotary conveyor without any gap.

6. The inspection machine according to claim 1, wherein said rotary conveyor and said intermediate conveyor overlap in the area of said feed conveyor.

7. The inspection machine according to claim 1, wherein said rotary conveyor comprises at least two endless conveying means which engage opposite sides of containers and are driven at different speeds.

8. The inspection machine according to claim 7, wherein an average speed calculated from the speeds of the conveying means of said rotary conveyor equals the corresponding speed of the two conveying means of said intermediate conveyor of said feed conveyor and said discharge conveyor.

9. The inspection machine according to claim 7, wherein trailing pulleys of said rotary conveyor and leading pulleys of said intermediate conveyor which are respectively located at a same side of said feed conveyor are coaxially arranged one on top of the other.

10. The inspection machine according to claim 9, wherein said trailing pulleys of said rotary conveyor and said leading pulley of said intermediate conveyor which are respectively positioned at the same side of said feed conveyor are mounted on a joint drive shaft and supported in a freely rotatable manner on said joint drive shaft.

11. The inspection machine according to claim 10, wherein intermediate conveyor trailing pulleys of said intermediate conveyor are mounted on intermediate conveyor drive shafts.

12. The inspection machine according to claim 7, wherein at each side of said feed conveyor said rotary conveyor comprises two endless, drivable conveying means which are positioned at a higher level and lower level, respectively, than said endless conveying means of said intermediate conveyor which is located at the same side.

13. The inspection machine according to claim 12, wherein said conveying means of said rotary conveyor are capable of engaginq upper and lower body portions of containers.

14. An inspection machine for containers, comprising:
a feed conveyor comprising an endless belt for feeding containers;
a discharge conveyor comprising an endless belt for discharging containers;
an intermediate conveyor which bridges a gap existing between said feed conveyor and said discharge conveyor, said intermediate conveyor comprising two driven endless conveying means for engaging opposite sides of containers and transferring without rotation, containers from said feed conveyor to said discharge conveyor;
a rotary conveyor arranged so that said intermediate conveyor follows said rotary conveyor along a length of said feed conveyor, without any gap between said intermediate conveyor and said rotary conveyor, said rotary conveyor comprising two driven endless conveying means for laterally engaging and rotating containers on said feed conveyor;
a first side inspection device arranged in an area of said feed conveyor upstream of said rotary conveyor for inspecting a first side of containers;
a second side inspection device downstream of said intermediate conveyor for inspecting a second side of containers; and
a bottom inspection device in an area of the gap for inspecting containers.

15. The inspection machine according to claim 14, wherein said rotary conveyor and said intermediate conveyor overlap in the area of said feed conveyor.

16. The inspection machine according to claim 14, wherein trailing pulleys of said rotary conveyor and leading pulleys of said intermediate conveyor are coaxially arranged one on top of the other.

17. The inspection machine of claim 16, wherein said trailing pulleys of said rotary conveyor and respective leading pulleys of said intermediate conveyor, which are respectively positioned at a same side of said feed conveyor are mounted on a joint drive shaft, such that said feed conveyor, said rotary conveyor and said intermediate conveyor are capable of simultaneously contacting a container at a position adjacent said joint drive shaft.

18. The inspection machine according to claim 14, wherein said two driven endless conveying means of said rotary conveyor are spaced on opposing sides of said feed conveyor, and each endless conveying means of said rotary conveyor comprises two endless, driven conveyor belts positioned above and below each respective said endless conveying means of said intermediate conveyor.

19. The inspection machine according to claim 14, wherein said feed conveyor, said discharge conveyor, said intermediate conveyor and said rotary conveyor travel in a horizontal direction.

* * * * *